United States Patent
Moberg et al.

(10) Patent No.: US 8,657,869 B2
(45) Date of Patent: Feb. 25, 2014

(54) MEDICAL SYSTEMS AND RELATED METHODS

(75) Inventors: John R. Moberg, Elk River, MN (US); Michael Gerdts, Big Lake, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1089 days.

(21) Appl. No.: 12/023,129

(22) Filed: Jan. 31, 2008

(65) Prior Publication Data
US 2008/0188920 A1    Aug. 7, 2008

Related U.S. Application Data

(60) Provisional application No. 60/887,974, filed on Feb. 2, 2007.

(51) Int. Cl.
*A61F 2/06* (2013.01)

(52) U.S. Cl.
USPC ........................................ 623/1.12

(58) Field of Classification Search
USPC .............. 623/1.11, 1.12, 1.23, 2.11; 606/191, 606/194, 198, 200
See application file for complete search history.

(56) References Cited

U.S. PATENT DOCUMENTS

| | | | |
|---|---|---|---|
| 5,501,654 A * | 3/1996 | Failla et al. | 600/204 |
| 5,843,091 A | 12/1998 | Holsinger | |
| 6,380,457 B1 | 4/2002 | Yurek et al. | |
| 2004/0098083 A1* | 5/2004 | Tran et al. | 623/1.11 |
| 2005/0027305 A1* | 2/2005 | Shiu et al. | 606/108 |
| 2005/0027345 A1 | 2/2005 | Horan et al. | |
| 2005/0080476 A1 | 4/2005 | Gunderson et al. | |
| 2005/0256562 A1* | 11/2005 | Clerc et al. | 623/1.11 |
| 2006/0009833 A1* | 1/2006 | Chobotov et al. | 623/1.11 |
| 2006/0074477 A1 | 4/2006 | Berthiaume et al. | |
| 2006/0190069 A1 | 8/2006 | Baker-Janis et al. | |

FOREIGN PATENT DOCUMENTS

| | | |
|---|---|---|
| JP | 2004275594 | 10/2004 |
| WO | 2004071352 A1 | 8/2004 |
| WO | WO 2005/112824 | 12/2005 |

OTHER PUBLICATIONS

International Search Report and Written Opinion; PCT/US2008/052555; mailed Jun. 12, 2008.

* cited by examiner

*Primary Examiner* — Ryan Severson
*Assistant Examiner* — Katherine M Shi
(74) *Attorney, Agent, or Firm* — Seager, Tufte & Wickhem LLC

(57) ABSTRACT

Medical systems and related methods are described. In some embodiments, the medical systems include an outer member defining a slot. In certain embodiments, the outer member at least partially surrounds an inner member, and the outer and inner members are configured so that an implantable medical endoprosthesis can be disposed between the outer and inner members.

21 Claims, 11 Drawing Sheets

MEDICAL SYSTEMS AND RELATED METHODS

CROSS-REFERENCE TO RELATED APPLICATIONS

This application claims the benefit of U.S. Provisional Application Ser. No. 60/887,974, filed on Feb. 2, 2007. The above-noted provisional application is incorporated by reference in its entirety.

TECHNICAL FIELD

This invention relates to medical systems and related methods.

BACKGROUND

Devices are known for delivering implantable endoprostheses, such as stents, into a body vessel. Devices of this kind often include a proximal portion that remains external to the body vessel during use and a distal portion that is inserted into the body vessel (e.g., through an incision). The proximal portion typically provides for manipulation of the device during use. The distal portion often includes an outer member slidably positioned about an inner member with an endoprosthesis disposed therebetween. Generally, the distal portion of the device is advanced through the body vessel to a treatment site (e.g., a stenosis or aneurysm). The outer member can then be retracted to allow the endoprosthesis to expand to engage a wall of the body vessel at the treatment site. Thereafter, the device is removed leaving the endoprosthesis engaged with the body vessel.

SUMMARY

In one aspect of the invention, a system, includes a connector secured to a housing of a handle assembly, an inner member secured to the connector, and an outer member at least partially surrounding the inner member. The outer member defines a slot configured so that a portion of the connector can be disposed within the slot, and the outer member and the inner member are configured so that an implantable medical endoprosthesis can be disposed between the outer member and the inner member.

In another aspect of the invention, a system includes a connector secured to a housing of a handle assembly and a rack secured to a sheath. The sheath is configured so that an implantable medical endoprosthesis can be disposed within the sheath, and the rack defines a longitudinal slot configured so that a portion of the connector can be disposed within the longitudinal slot such that the rack and the sheath can be longitudinally displaced relative to the handle and the connector.

In an additional aspect of the invention, a method includes retracting an outer member relative to an inner member. A portion of a connector to which the inner member is secured is disposed within a slot defined by the outer member as the outer member is retracted relative to the inner member, and the outer member and the inner member are configured so that an implantable medical endoprosthesis can be disposed between the outer member and the inner member.

Embodiments can include one or more of the following features.

In some embodiments, the outer member is retractable relative to the inner member.

In certain embodiments, a distal end of the slot, upon contacting the connector, substantially prevents further retraction of the outer member relative to the inner member.

In some embodiments, the system further includes a stop secured to the outer member, and the stop is configured to contact the connector so that displacement of the outer member and the inner member can be limited.

In certain embodiments, the stop includes an annular ring.

In some embodiments, the outer member includes a proximal portion and a distal portion, and the proximal portion includes radially extending teeth.

In certain embodiments, the handle includes a rotatable knob configured to engage the radially extending teeth of the first portion of the outer member such that the outer member can be retracted by rotating the rotatable knob.

In some embodiments, the slot extends from a proximal end of the proximal portion to a location proximal to a distal end of the proximal portion.

In certain embodiments, the slot extends from a proximal end of the proximal portion to a distal end of the proximal portion.

In some embodiments, the slot extends into the distal portion of the outer member.

In certain embodiments, the proximal portion of the outer member includes a tubular rack and the distal portion of the outer member includes a sheath, and the tubular rack is secured to the sheath.

In some embodiments, the sheath and the inner member are configured so that an implantable medical endoprosthesis can be disposed between the sheath and the inner member.

In certain embodiments, at least a portion of the sheath can be retracted into the handle assembly.

In some embodiments, the outer member extends through the handle assembly, and a pull grip is secured to the outer member proximal to the handle assembly.

In certain embodiments, the connector includes a tubular portion at least partially surrounding the inner member.

In some embodiments, the connector further includes a rib portion securing the tubular portion to the handle assembly, and the slot is configured so that the rib portion of the connector can extend radially through the slot.

In certain embodiments, the slot is configured so that a guide wire can pass radially through the slot.

In some embodiments, during use, the guide wire passes radially through the slot at a location proximal to the handle assembly.

In certain embodiments, the system further includes an implantable medical endoprosthesis disposed between the outer member and the inner member.

In some embodiments, the implantable medical endoprosthesis is a self-expanding stent.

In certain embodiments, the rack and the sheath can be longitudinally displaced to an extent such that a distal end of the rack is proximal to a distal end of the handle assembly.

In some embodiments, the rack and the sheath can be longitudinally displaced to an extent such that a portion of the sheath extends into the handle assembly.

In certain embodiments, the longitudinal slot is configured so that a guide wire can pass radially through the longitudinal slot.

In some embodiments, during use, the guide wire passes radially through the longitudinal slot at a location proximal to the handle assembly.

In certain embodiments, the connector is secured to a housing of a handle assembly.

In some embodiments, the method further includes passing a guide wire through the slot.

In certain embodiments, the outer member is at least partially disposed within a handle assembly and the guide wire is passed through the slot at a location proximal to the handle assembly.

In some embodiments, retracing the outer member relative to the inner member allows an implantable medical endoprosthesis disposed between the outer member and the inner member to expand.

In certain embodiments, retracing the outer member relative to the inner member includes rotating a rotatable knob engaged with the outer member.

In some embodiments, retracing the outer member relative to the inner member includes pulling a pull member secured to a proximal end region of the outer member in a proximal direction.

In certain embodiments, the outer member includes a sheath that can contain an implantable medical endoprosthesis therein and the connector is secured to a housing of a handle assembly, and retracting the outer member relative to the inner member includes retracting a portion of the sheath into the handle assembly.

In some embodiments, the connector is secured to a housing of a handle assembly, and when the outer member is retracted relative to the inner member, a portion of the outer member extends proximally beyond a proximal end of the handle assembly.

Embodiments can include one or more of the following advantages.

In some embodiments, the outer member is configured to exit the proximal end of the handle assembly when retracted during use. As a result, the length of the handle assembly can be reduced relative to the length of handle assemblies of certain conventional systems that are designed for the same type of use.

In certain embodiments, a distal portion of the outer member (e.g., the outer sheath of the outer member) can be retracted into the handle assembly during use. Consequently, the overall length of the system can be reduced relative to certain conventional systems designed for the same type of use.

In some embodiments, the slot of the outer member (e.g., the slot of the rack of the outer member) is configured so that a guide wire can extend radially through the slot during use. As a result, the guide wire can remain exposed and accessible to the user throughout the procedure (e.g., throughout the procedure for deploying the stent). This arrangement can improve the ease with which the user grasps the guide wire during use of the system. Further, in some instances, this arrangement can permit the system to be used with guide wires of a conventional length (e.g., 260 centimeters) even when performing procedures that typically require the use of longer systems (e.g., when delivering long stents to blood vessels in remote portions of the body, such as lower extremities of the body).

In certain embodiments, the pull grip is secured to the outer member at a location proximal to handle. This arrangement can permit the outer member to be retracted through the handle assembly without interference between the pull grip and the handle.

Other aspects, features, and advantages are in the description, drawings, and claims.

DETAILED DESCRIPTION

In certain aspects of the invention, a system (e.g., a stent delivery system) includes an outer member (e.g., an outer tubular assembly) that includes a longitudinal slot. An inner member (e.g., an inner tubular member) extends within the outer member and is attached to a housing of a handle assembly by a connector. A portion of the connector (e.g., a rib portion of the connector) extends through the slot of the outer member. This arrangement can, for example, allow a user to retract the outer member relative to the inner member and the connector. In some embodiments, the housing and the outer member are configured to permit the outer member to extend proximally beyond the proximal end of the handle assembly when the outer member is retracted relative to the inner member and the connector. In certain embodiments, during use, a guide wire can extend radially through the slot in the outer member proximal to the handle assembly, allowing the user to conveniently grasp the guide wire even when the outer member is retracted proximally beyond the proximal end of the handle assembly.

Figure 1:
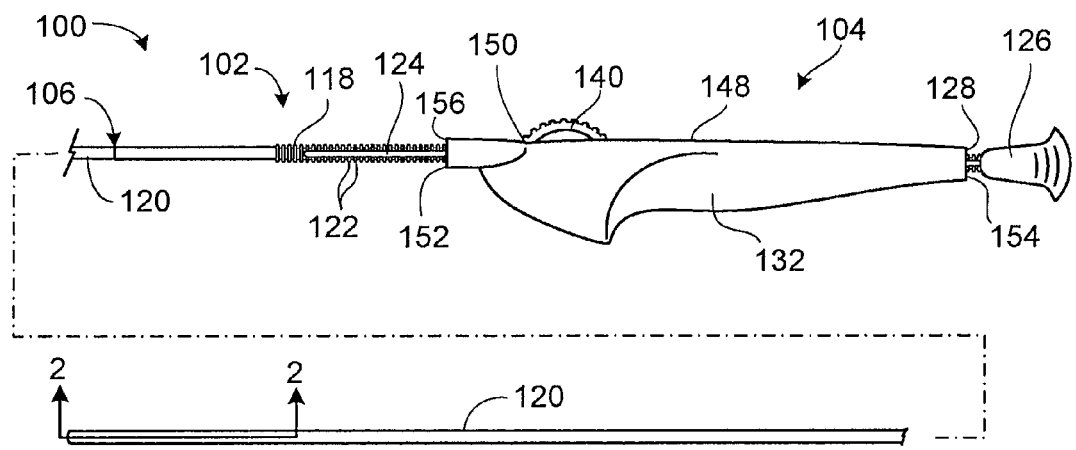
FIG. 1 is a broken, side view of a stent delivery system.
Figure 2:
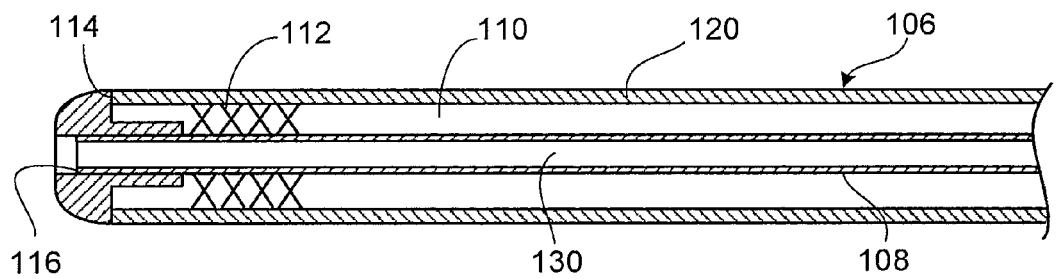
FIG. 2 is a cross-sectional view of a distal region of the catheter assembly of the stent delivery system of FIG. 1, taken along line 2-2 in FIG. 1.

Referring to FIGS. 1 and 2, a stent delivery system 100 includes a catheter assembly 102 and a handle assembly 104. Catheter assembly 102 includes an outer tubular assembly 106 and an inner tubular member 108 extending through a lumen 110 formed by outer tubular assembly 106. A self-expanding stent 112 is disposed between outer tubular assembly 106 and inner tubular member 108, near distal ends 114, 116 of outer tubular assembly 106 and inner tubular member 108. During use, as described in more detail below, a distal portion of catheter assembly 102 can be disposed within a body vessel (e.g., blood vessel) of a patient, and outer tubular assembly 106 can be retracted proximally relative to inner tubular member 108 to deploy stent 112 within the body vessel of the patient.

Figure 3:
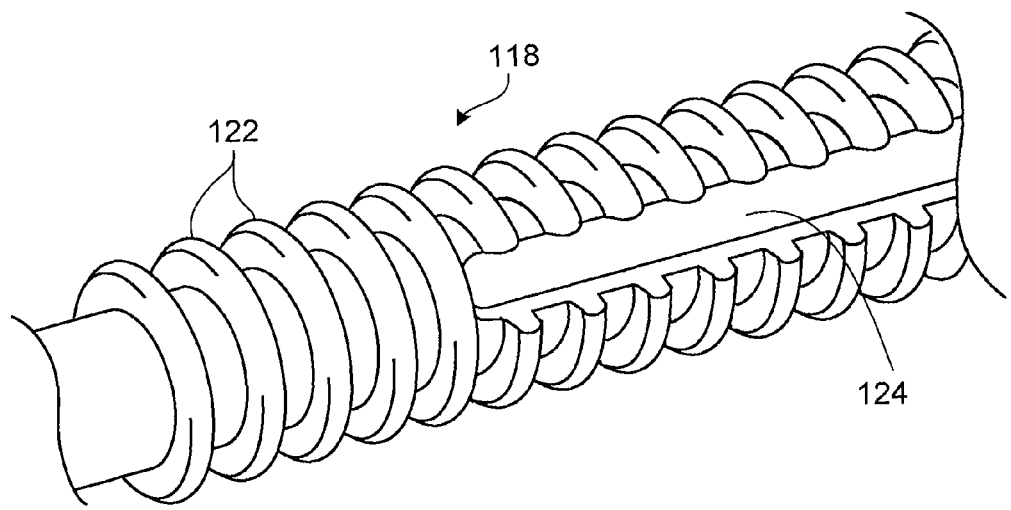
FIG. 3 is a partial, perspective view of a distal region of the rack of the stent delivery system of FIG. 1.

Outer tubular assembly 106 of catheter assembly 102 includes a tubular rack 118 attached to the proximal end of an outer sheath 120. FIG. 3 illustrates a perspective view of a distal region of tubular rack 118. Referring to FIGS. 1 and 3, tubular rack 118 includes multiple radially extending teeth 122 that are axially spaced along tubular rack 118. Tubular rack 118 can have any of various lengths, depending on the distance that tubular rack 118 and outer sheath 120 are to be retracted in order to carry out a treatment (e.g., to deploy stent 112). In some embodiments, tubular rack 118 has a length of about two inches to about 12 inches (e.g., about four inches to about eight inches). In some embodiments, tubular rack 118 has a length of about 12 inches or greater.

A longitudinal slot 124 is formed in the sidewall of tubular rack 118. Slot 124 provides a radial passage from lumen 110 to an area surrounding tubular rack 118. Slot 124 extends from the proximal end of tubular rack 118 to a location proximal to the distal end of tubular rack 118. The length of slot 124 can dictate the longitudinal distance by which tubular rack 118 and outer sheath 120 can be retracted during use. In some embodiments, slot 124 has a length of about two inches to about 12 inches (e.g., about four inches to about eight inches). In some embodiments, slot 124 has a length of about 12 inches or greater. In certain embodiments, slot 124 has a width that is sufficient to allow a guide wire to pass radially through tubular rack 118 via slot 124. Slot 124 can, for example, have a width of about 0.030 inch to about 0.090 inch (e.g., about 0.070 inch).

Tubular rack 118 can include (e.g., can be formed of) any of various materials. In some embodiments, tubular rack 118 includes one or more polymeric materials, such as polycarbonate, acrylonitrile butadiene styrene (ABS), and blends thereof. Alternatively or additionally, tubular rack 118 can include one or more metals or alloys, such as stainless steel. In certain embodiments, tubular rack 118 includes an inner layer formed of a metal, such as stainless steel, surrounded by an outer layer formed of a polymeric material, such as acrylonitrile butadiene styrene (ABS). Slot 124 can be formed in tubular rack 118 using any of various techniques. In some embodiments, for example, tubular rack 118 is molded (e.g., injection molded) or cast (e.g., die cast) in a manner to form slot 124. Alternatively or additionally, a circumferentially continuous tubular rack can be formed and then material can be removed from the circumferentially continuous tubular rack (e.g., by cutting or etching) to form slot 124.

Referring again to FIG. 1, a pull grip 126 is provided on a proximal end region of tubular rack 118. Pull grip 126 is located proximal to a proximal end 128 of handle assembly 104 and includes radially extending projections that can be grasped by the user during use. In some embodiments, pull grip 126 is a discrete component that is secured to tubular rack 118. In such embodiments, pull grip 126 can, for example, be adhesively attached, thermally bonded, welded, etc. to an outer surface of the proximal end region of tubular rack 118. Alternatively, pull grip 126 can be integrally formed (e.g., molded) with tubular rack 118.

As noted above, the distal end of tubular rack 118 is attached to the proximal end of outer sheath 120. Outer sheath 120 is configured to contain stent 112 in a compressed state prior to deployment. In certain embodiments, outer sheath 120 includes a multi-layer construction. In some embodiments, for example, outer sheath 120 includes an inner layer formed of polytetra-fluoroethylene (PTFE), a middle layer formed of a stainless steel mesh, and an outer layer formed of nylon 12 and/or polyether block amide (e.g., PEBAX). Any of various techniques can be used to attach tubular rack to outer sheath. For example, tubular rack and outer sheath can be adhesively bonded, thermally bonded, welded, etc.

Referring again to FIG. 2, inner tubular member 108 extends within lumen 110 of outer tubular assembly 106. Inner tubular member 108 forms a guidewire lumen 130 that extends from the proximal end of inner tubular member 108 to the distal end of inner tubular member 108. A proximal end region of inner tubular member 108 extends into and is secured to a housing 132 of handle assembly 104, as shown in FIG. 4, which is discussed below.

Inner tubular member 108 and outer sheath 120 can be flexible along their lengths to allow catheter assembly 102 to be deflected and articulated, e.g., to traverse a tortuous blood vessel. Inner tubular member 108 and outer sheath 120 can, for example, include one or more compliant polymeric materials. Examples of suitable polymeric materials include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), high-density polyethylene (HDPE), low-density polyethylene (LDPE), polyamides (e.g., Vestamid® and combinations of these materials. In some embodiments, inner tubular member 108 and outer sheath 120 include one or more silicones. In certain embodiments (e.g., when it is desirable to reduce the force used to retract outer sheath 120), inner tubular member 108 and/or outer sheath 120 can be made of a material having a relatively low coefficient of friction (e.g., a fluoropolymer or a silicone). Examples of fluoropolymers include PTFE and FEP. Alternatively or additionally, inner tubular member 108 and/or outer sheath 120 can be made of a material that includes a lubricious additive (e.g., a fluoropolymer, a silicone, an ultrahigh molecular weight polyethylene, an oil, or blends thereof).

Figure 4:
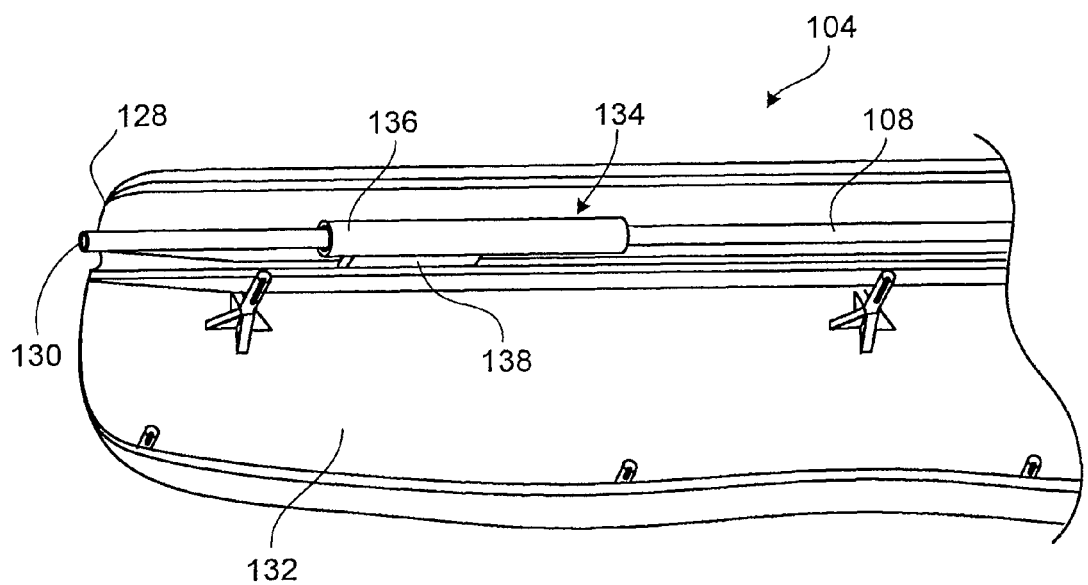
FIG. 4 illustrates a connection between the inner member of the catheter assembly of the stent delivery system of FIG. 1 and the housing of the handle assembly of the stent delivery system of FIG. 1.

FIG. 4 illustrates a section of handle assembly 104 in a partially assembled state with one of the sides of housing 132 removed to show how inner tubular member 108 is secured to housing 132. As shown in FIG. 4, inner tubular member 108 is secured to an inner surface of housing 132 by a connector 134. As a result, inner tubular member 108 is axially fixed relative to housing 132. Inner tubular member 108 extends proximally through connector 134 to proximal end 128 of handle assembly 104. As a result, guide wire lumen 130, which extends to the proximal end of inner tubular member 108 provides a path through which a guide wire can extend proximally beyond housing 132.

Connector 134 includes a tubular portion 136 and a rib portion 138. A portion of inner tubular member 108 is disposed in tubular portion 136. Rib portion 138 extends radially from tubular portion 136 and is secured to the side wall of housing 132. An outer surface of inner tubular member 108 is secured to an inner surface of tubular portion 136. Any of various techniques can be used to secure inner tubular member 108 to tubular portion 136. In certain embodiments, for example, inner tubular member 108 is adhesively bonded to tubular portion 136. Alternatively or additionally, inner tubular member 108 can be thermally bonded or welded to tubular portion 136. Rib portion 138 of connector 134 can be secured to housing 132 of handle assembly 104 using any of various techniques. In some embodiments, for example, rib portion 138 of connector 134 is insert molded along with housing 132 of handle assembly 104 in order to secure connector 134 to housing 132. Alternatively or additionally, one or more other techniques can be used to secure rib portion 138 of connector 134 to housing 132 of handle assembly 104. For example, rib portion 138 of connector 134 can be adhesively attached, welded, and/or thermally bonded to housing.

In some embodiments, connector 134 includes (e.g., is formed of) one or more metals or alloys. For example, connector 134 can include stainless steel. Alternatively or additionally, connector 134 can include one or more polymeric materials, such as polycarbonate, acrylonitrile butadiene styrene (ABS), and blends thereof. In certain embodiments, tubular portion 136 and rib portion 138 of connector 134 are integrally formed with one another. In such embodiments, for example, connector 134 can be die cast, injection molded, etc. Alternatively, tubular portion 136 and rib portion 138 can be separately formed components that are attached (e.g., bonded, welded, etc.) to one another.

Figure 5:
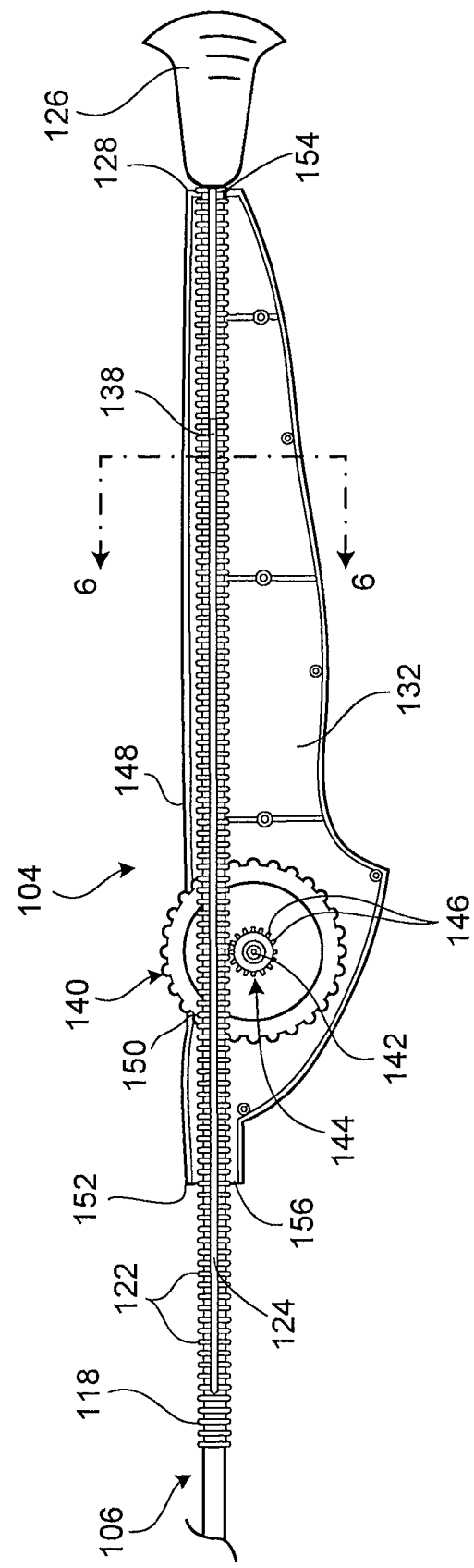
FIG. 5 is a side view of the handle assembly of the stent delivery system of FIG. 1 in an operative configuration with the near side of its housing removed to expose certain interior components of the handle assembly.

FIG. 5 illustrates a side view of handle assembly 104 in an operable configuration with the near side of its housing 132 (i.e., the side of housing 132 to which connector 134 is secured, as shown in FIG. 4) removed to expose certain interior components of handle assembly 104. As shown in FIG. 5, a rotatable knob 140 is rotatably mounted to housing 132. Rotatable knob 140 includes a pin 142 that extends laterally from a side surface of rotatable knob 140 and can be disposed within a cylindrical recess defined by the side wall of housing 132. This configuration allows rotatable knob 140 to be rotated relative to housing 132. Alternatively or additionally, any of various other configurations that allow rotatable knob 140 to be rotated relative to housing 132 can be used. Rotatable knob 140 also includes a gear 144 that laterally extends from the side surface of rotatable knob 140. Gear 144 includes multiple circumferentially spaced teeth 146 that extend radially from a peripheral surface of gear 144. A top wall 148 of housing 132 includes an aperture 150 through which an upper portion of rotatable knob 140 protrudes to allow rotatable knob 140 to be rotated by the thumb of a user.

In the operable configuration, as shown in FIG. 5, inner tubular member 108 (shown in FIG. 4) and tubular rack 118 of catheter assembly 102 extend within a cavity formed by housing 132 of handle assembly 104. Teeth 122 of tubular rack 118 mate with teeth 146 of gear 144. Thus, tubular rack 118 can be axially displaced by rotating rotatable knob 140. Tubular rack 118 extends entirely through handle assembly 104 such that, in an initial configuration, a proximal region of tubular rack 118 extends proximal to a proximal end 128 of handle assembly 104 and a distal region of tubular rack 118 extends distal to distal end 152 of handle assembly 104. Housing 132 of handle assembly 104 includes proximal and distal openings 154, 156 that provide sufficient clearance for tubular rack 118 and outer sheath 120 to pass through the openings and thus move axially through housing 132 without substantial interference.

Figure 6:
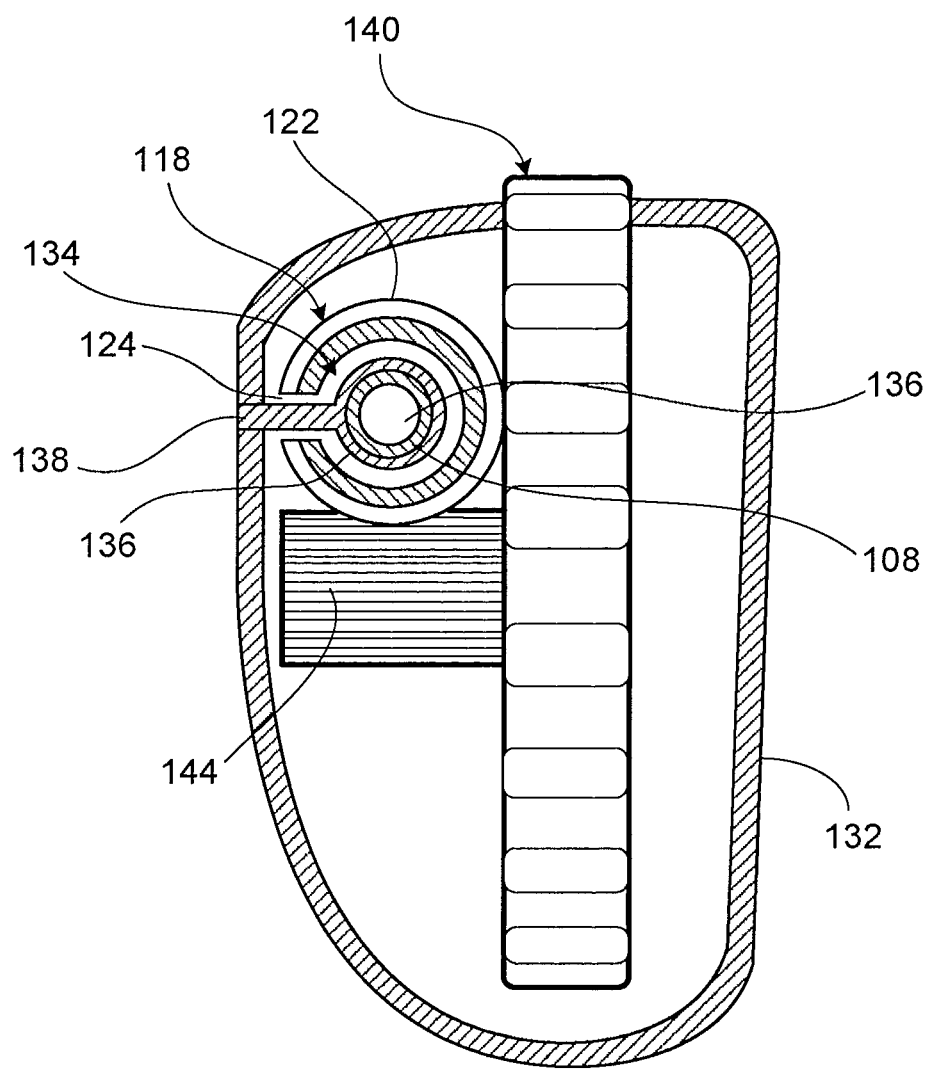
FIG. 6 is a cross-sectional view of the handle assembly of the stent delivery system of FIG. 1 in a fully assembled configuration, taken along line 6-6 in FIG. 5.

FIG. 6 illustrates a cross-sectional view of handle assembly 104 in a fully assembled configuration (i.e., with the near side of housing 132 in place). As shown in FIG. 6, rib portion 138 of connector 134 extends radially through slot 124 of tubular rack 118. Slot 124 is configured (e.g., sized and shaped) so that tubular rack 118 can be retracted relative to connector 134 while rib portion 138 extends through slot 124. The width of slot 124 can, for example, be greater than (e.g., about 0.005 inch to about 0.010 inch greater than) the width of rib portion 138.

Referring to FIGS. 5 and 6, slot 124 extends from the proximal end of tubular rack 118 to a location proximal to the distal end of tubular rack 118. As a result, tubular rack 118 can be proximally retracted until rib portion 138 of connector 134 abuts the distal end of slot 124 (e.g., the surface of tubular rack 118 that defines the distal end of slot 124). Due to the arrangement of slot 124, when outer tubular assembly 106 is fully retracted, the distal end of tubular rack 118 is located proximal to distal end 152 of handle assembly 104 and a portion of outer sheath 120 is retracted into housing 132 of handle assembly 104. Because the configuration of system 100 allows the proximal end of tubular rack 118 to extend proximally beyond proximal end 128 of handle assembly 104, the length of handle assembly 104 need not be dictated by the distance that tubular rack 118 needs to be retracted to perform a particular treatment (e.g., to deploy a stent of a particular length). As a result, handle assembly 104 can be shortened relative to certain handle assemblies of conventional stent delivery systems (e.g., stent delivery systems designed to deliver long stents). In addition, because a portion of outer sheath 120 can be retracted into housing 132 of handle assembly 104, the overall length of system 100 can be shortened relative to certain conventional stent delivery systems (e.g., stent delivery systems designed to deliver long stents).

Outer sheath 120 can be retracted using either rotatable knob 140 or pull grip 126. To retract outer sheath 120 using rotatable knob 140, the user rotates rotatable knob 140 in a clockwise direction (in the view illustrated in FIG. 5). The rotation of gear 144 causes teeth 146 of gear 144 to engage teeth 122 of tubular rack 118, and thereby proximally displace tubular rack 118. Because tubular rack 118 is secured to outer sheath 120, the proximal displacement of tubular rack 118 results in retraction of outer sheath 120. To retract outer sheath 120 using pull grip 126, the user grasps pull grip 126 and pulls pull grip 126 in the proximal direction.

Figure 7A:
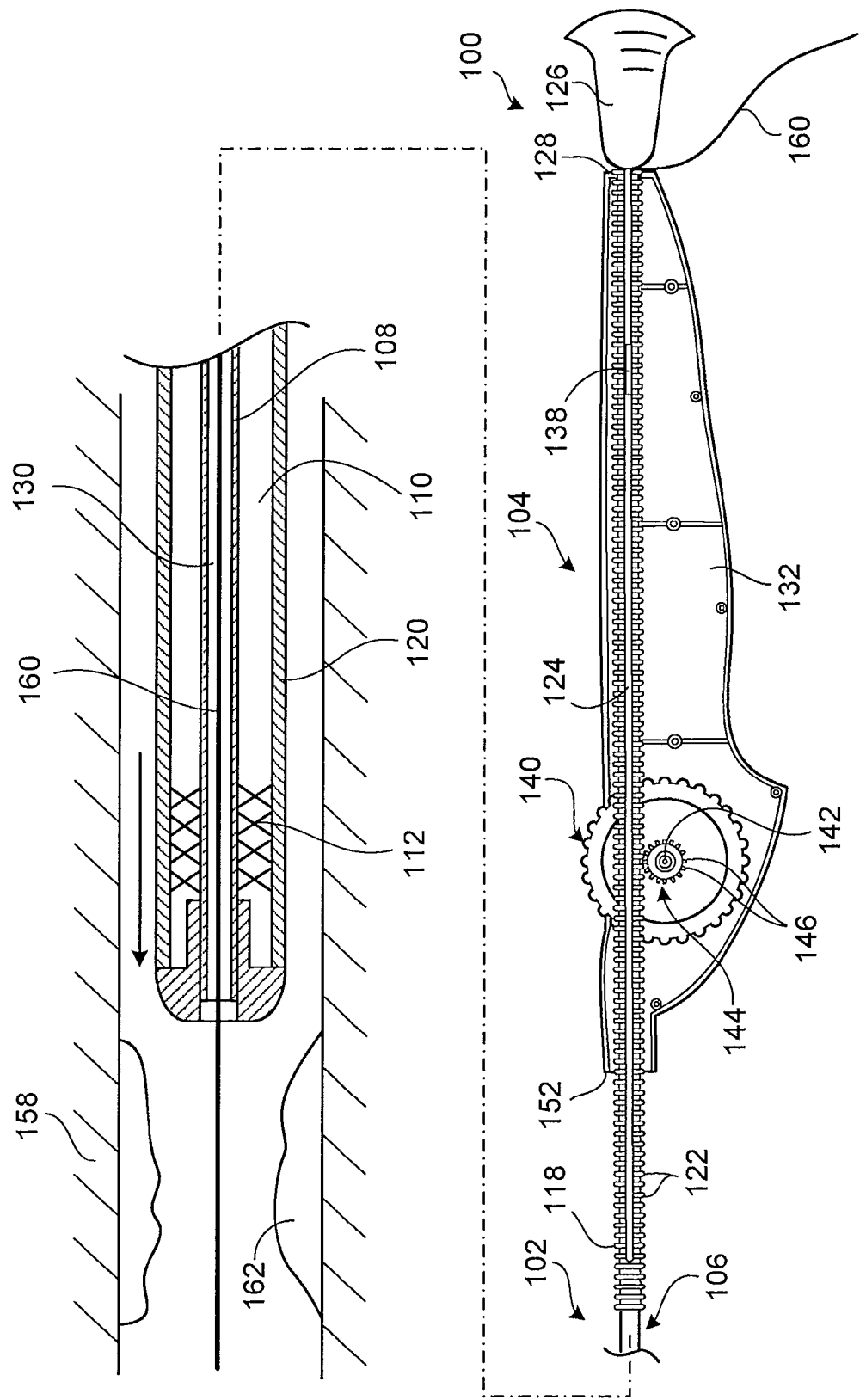
FIGS. 7A-7D illustrate a method of using the stent delivery system of FIG. 1 to implant a self-expanding stent within a blood vessel.

FIGS. 7A-7D illustrate a method of using system 100 to implant stent 112 within a blood vessel 158 of a patient. Referring to FIG. 7A, a guide wire 160 is first inserted into blood vessel 158, and catheter assembly 102 is passed over guide wire 160 such that guide wire 160 becomes disposed within guide wire lumen 130 of inner tubular member 108. Guide wire 160 exits the proximal end of inner tubular member 108 and extends radially through slot 124 of tubular rack 118, proximal to handle assembly 104. A distal portion of catheter assembly 102 is navigated through blood vessel 158 and toward an occluded region 162 of blood vessel 158 by passing catheter assembly 102 over guide wire 160.

Figure 7B:
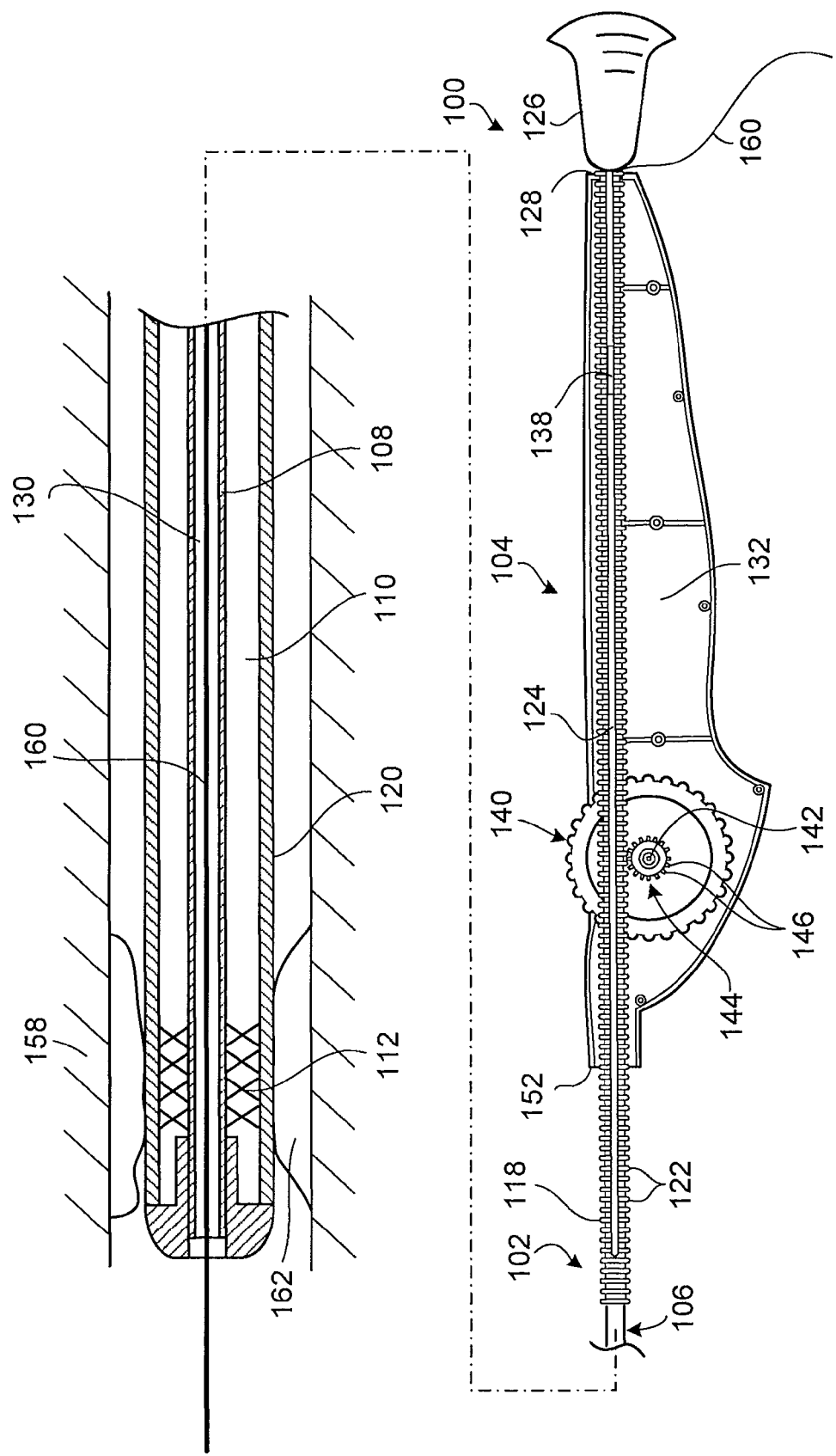

The distal portion of catheter assembly 102 is navigated through blood vessel 158 until the stent-carrying portion of catheter assembly 102 is positioned within occluded region 162, as shown in FIG. 7B. Fluoroscopy or any of various other imaging techniques can be used to help the user position the stent-carrying portion of catheter assembly 102 within occluded region 162.

Figure 7C:
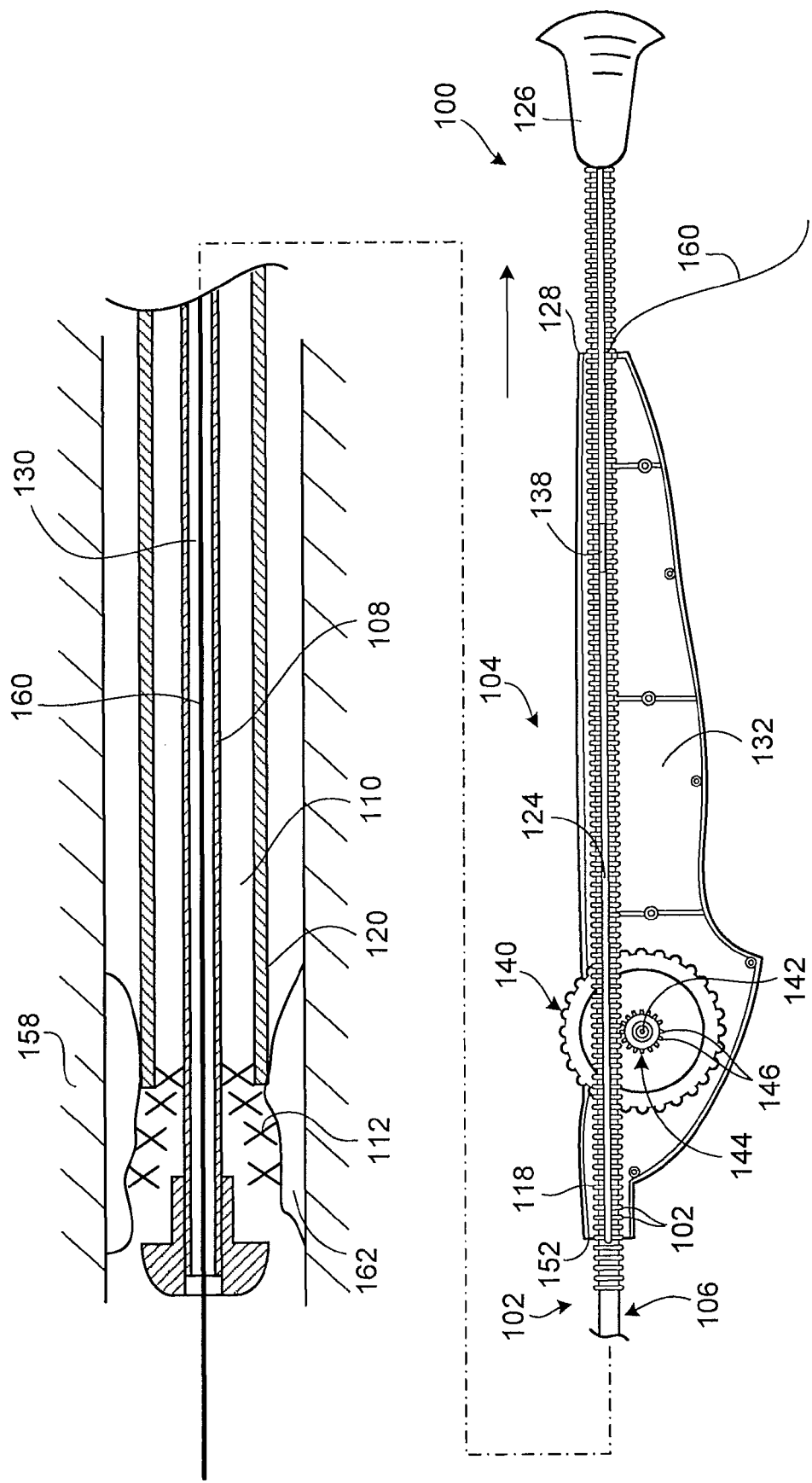

Referring to FIG. 7C, after positioning the stent-carrying portion of catheter assembly 102 within occluded region 162, tubular rack 118 and outer sheath 120 are retracted an initial distance relative to inner tubular member 108 by rotating rotatable knob 140 in a clockwise direction (in the view illustrated in FIG. 7C). This initial retraction of outer sheath 120 allows a distal portion of stent 112 to self-expand within occluded region 162 and contact a wall of body vessel 158. As tubular rack 118 is retracted, the proximal end of tubular rack 118 moves proximally away from proximal end 128 of handle assembly 104. The amount of guide wire 160 exposed to the user does not significantly change as tubular rack 118 is retracted because guide wire 160 extends radially through slot 124 of tubular rack 118. Thus, the ability of the physician to grasp guide wire 160 is not substantially altered by retraction of tubular rack 118. Consequently, the increased overall length of system 100 that results from tubular rack 118 being retracted proximal to handle assembly 104 does not generally require the use of longer guide wires.

Figure 7D:
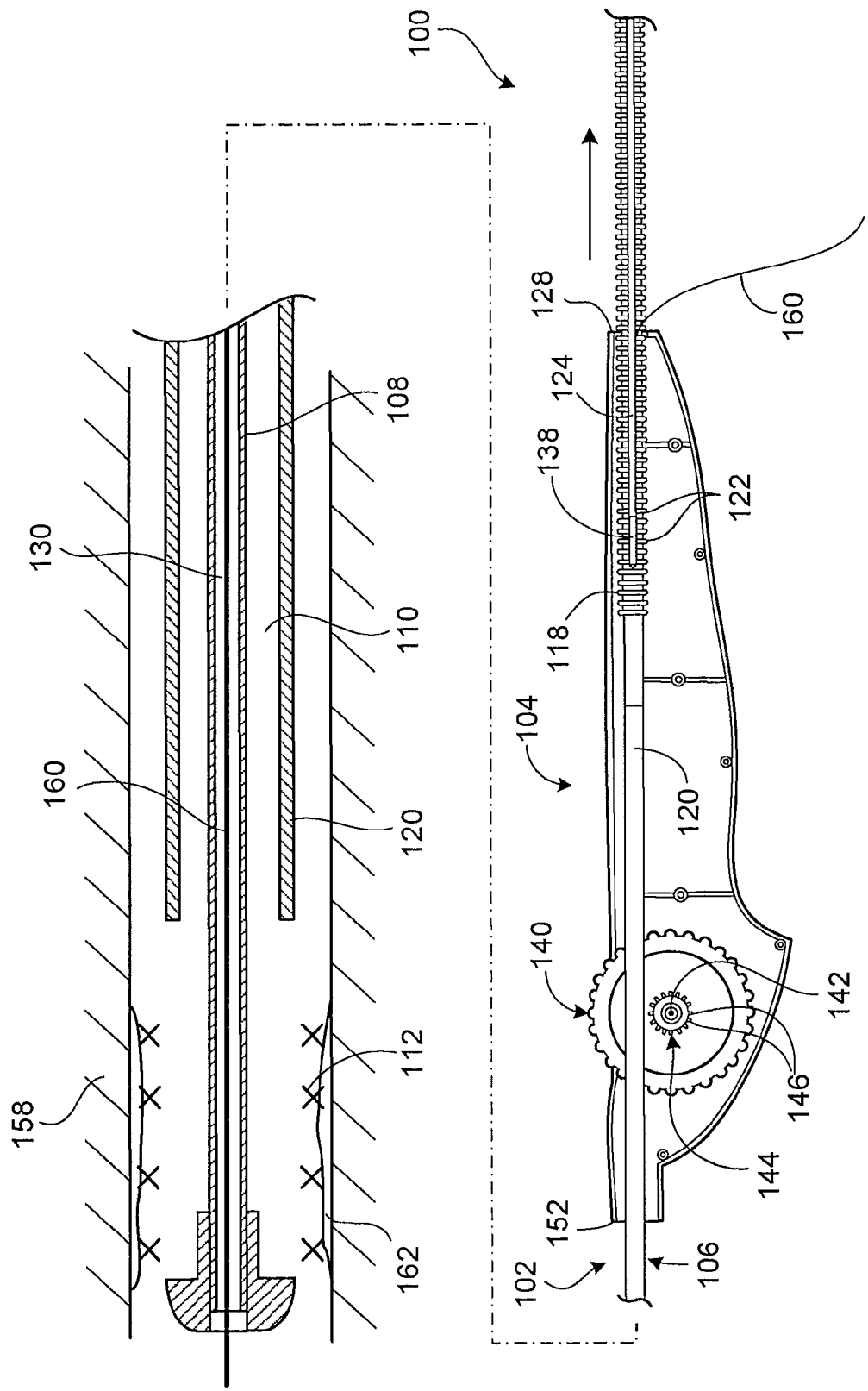

Referring to FIG. 7D, the user subsequently pulls proximally on pull grip 126 until rib portion 138 of connector 134 abuts the distal end of slot 124, preventing further retraction of tubular rack 118 and outer sheath 120. In this fully retracted position, the entire length of tubular rack 118 is proximal to distal end 152 of handle assembly 104 and a proximal portion of outer sheath 120 resides within the cavity formed by housing 132 of handle assembly 104. Pull grip 126 generally permits the user to retract outer sheath 120 more rapidly than rotatable knob 140. In addition, pull grip 126 permits the user to retract outer sheath 120 even when the portion of tubular rack 118 that includes teeth 122 has been retracted proximally beyond rotatable knob 140, rendering rotatable knob 140 incapable of retracting outer sheath 120. As outer sheath 120 is retracted past the proximal end of stent 112, the full length of stent 112 is allowed to self-expand to a larger diameter and contact the blood vessel wall. Even when tubular rack 118 is fully retracted, guide wire 160 remains exposed to the user because guide wire 160 extends radially through slot 124 of tubular rack 118 slightly proximal to proximal end 128 of handle assembly 104. This feature can be particularly beneficial for systems that are used to deliver and deploy long stents, where the overall length of the system when the rack is fully retracted can exceed the length of a conventional guide wire (e.g., a 260 centimeter guide wire).

After deploying stent 112, system 100 and guide wire 160 are withdrawn from blood vessel 158, leaving stent 112 implanted in blood vessel 158.

The above-described method can be performed in any of various types of blood vessels. In some cases, the above-described method is used to treat conditions in blood vessels that require the use of long stents (e.g., stents having a length greater than about 80 millimeters, greater than about 100 millimeters, greater than about 150 millimeters, greater than about 200 millimeters, about 80 millimeters to about 250 millimeters). For example, system 100 can be used to treat conditions in superficial femoral arteries (SFAs), biliary vessels, and/or brachial vessels. As discussed above, the ability to retract tubular rack 118 proximally beyond handle assembly 104 and to retract outer sheath 120 partially into handle assembly 104 permits the length of handle assembly 104 and, in some cases, the overall length of system 100 to be reduced relative to certain conventional systems designed to treat similar conditions. This reduced length can improve the feel for the user, especially with systems used to deliver long stents. In addition, because guide wire 160 can extend through slot 124 in tubular rack 118 slightly proximal to handle assembly 104, a greater portion of guide wire 160 remains exposed and accessible to the user during use. As a result, the delivery of long stents can, in some instances, be carried out without having to use a guide wire of increased length. In many cases, for example, a conventional 260 centimeter guide wire can be used with system 100 to deliver and deploy long stents within relatively remote blood vessels (e.g., blood vessels in the lower extremities of a patient).

While certain embodiments have been described, other embodiments are possible.

As an example, while slot 124 has been described as extending from the proximal end of tubular rack 118 to a location proximal to the distal end of tubular rack 118, other arrangements are possible. In some embodiments, for example, slot 124 extends the entire length of tubular rack 118, from the proximal end of tubular rack 118 to the distal end of tubular rack 118. In such embodiments, the proximal end of outer sheath 120 can prevent further retraction of tubular rack 118 and outer sheath 120 upon abutting rib portion 138 of connector 134. Alternatively or additionally, slot 124 can extend distally beyond tubular rack 118 and into outer sheath 120. Such an arrangement can permit outer sheath 120 to be retracted a greater distance. This arrangement can, for example, allow a greater length of outer sheath 120 to be retracted into housing 132 of handle assembly 104. Thus, stents of increased length can be deployed without substantially increasing the length of tubular rack 118.

As another example, while tubular rack 118 has been described as extending through the entire length of handle assembly 104, in certain embodiments, prior to retraction, tubular rack 118 extends only into a distal portion of handle assembly 104. In such embodiments, for example, tubular rack 118 is equipped with a pull grip configured to slide within handle assembly 104 and exit proximal end 128 of handle assembly 104 when tubular rack is retracted (e.g., by rotating rotatable knob 140). In certain embodiments, housing 132 of handle assembly 104 defines a longitudinal slot through which the radially extending pull grip extends when tubular rack 118 is retracted. Alternatively, tubular rack 118 can include no pull grip, allowing the full length of tubular rack 118 to pass through the cavity defined by housing 132 of handle assembly 104. These arrangements can result in a shorter overall length of the system when tubular rack 118 is fully retracted.

As a further example, while inner tubular member 108 has been described as extending to proximal end 128 of handle assembly 104, inner tubular member 108 need not extend all the way through handle assembly 104. In some embodiments, for example, the proximal end of inner tubular member 108 is attached to connector 134. In such embodiments, connector 134 can be arranged to extend to proximal end 128 of handle assembly 104 to ensure that a guide wire can be fed through the entire length of handle assembly 104 (e.g., through guide wire lumen 130 of inner tubular member 108 and through tubular portion 136 of connector 134) without impediment. The lumen of connector 134 can, for example, serve as an extension of guide wire lumen 130 to guide the guide wire to proximal opening 154 in housing 132 of handle assembly 104.

As an additional example, while connector 134 has been described as including a tubular portion 136 that receives inner tubular member 108 and a rib portion 138 that is secured to housing 132 of handle assembly 104, connectors having other configurations can alternatively or additionally be used. In some embodiments, for example, rather than including a tubular portion, connector 134 includes a c-channel member that is secured to inner tubular member 108 and rib portion 138. Alternatively or additionally, rib portion 138 can be directly attached (e.g., adhesively bonded, thermally bonded, welded, etc.) to inner tubular member 108 to secure inner tubular member 108 to housing 132.

As another example, in some embodiments, a stop member (e.g., a clip) is disposed on tubular rack 118 and/or outer sheath 120. The stop member can, for example, be configured to abut connector 134 when tubular rack 118 and outer sheath 120 are retracted a predetermined distance. As a result, the stop member can prevent retraction of tubular rack 118 and outer sheath 120 beyond the predetermined distance. In certain embodiments, the stop member is adjustable such that the stop member can be fixed to tubular rack 118 and/or outer sheath 120 at any of a number of locations. In such embodiments, the maximum distance by which tubular rack 118 and outer sheath 120 can be retracted can be adjusted by altering the position of the stop member along tubular rack 118 and/or outer sheath 120. The stop can, for example, be a c-shaped clip that clamps onto tubular rack 118 between adjacent teeth 122. Alternatively or additionally, the stop can be an annular ring that surrounds and is attached to tubular rack 118 and/or outer sheath 120.

As an additional example, while tubular rack 118 has been shown as including a toothed portion that extends all the way to the proximal end of tubular rack 118, in certain embodiments, a proximal region of the tubular rack (e.g., the region of the tubular rack proximal to rotatable knob 140 in the initial configuration) includes no teeth. The lack of teeth on the proximal region of tubular rack does not impact the ability of rotatable knob 140 to retract the tubular rack because the proximal region of the tubular rack does not extend through the region of handle assembly 104 including rotatable knob 140 during retraction. In certain instances, the lack of teeth on the proximal region of the tubular rack can improve the ease with which the tubular rack moves through proximal opening 154 in handle assembly 104.

Figure 8:
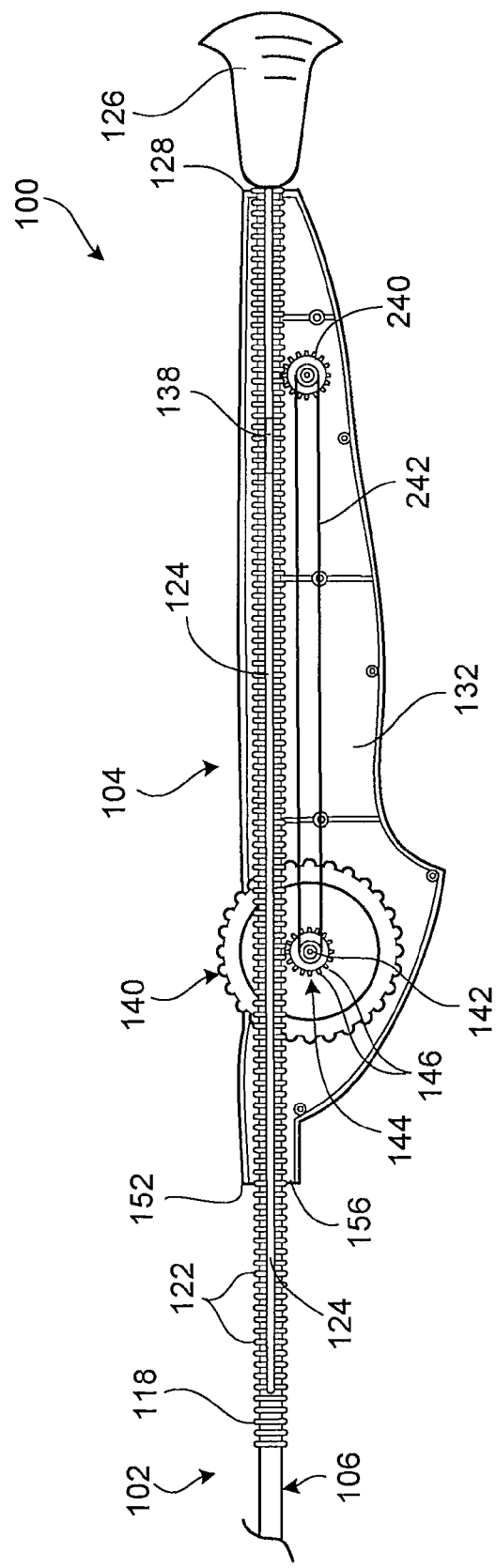
FIG. 8 is a side view of a handle assembly of a stent delivery system in an operative configuration with the near side of its housing removed to expose certain interior components of the handle assembly.

As a further example, while handle assembly 104 has been described as including a single rotatable knob 140, handle assembly can alternatively include multiple rotatable knobs. In some embodiments, for example, in addition to rotatable knob 140, handle assembly 104 can include a proximal rotatable knob located near proximal end 128 of handle assembly 104. In such embodiments, the proximal rotatable knob can be used to retract tubular rack 118 after the portion of tubular rack 118 including teeth 122 has been retracted proximally beyond rotatable knob 140. This arrangement can provide the user with mechanical advantage throughout the retraction process. Alternatively or additionally, as shown in FIG. 8, rotatable knob 140 can be operatively connected to a more proximal gear 240 via a pulley system 242. Teeth of proximal gear 242 can be configured to engage teeth 122 of tubular rack 118. As rotatable knob 140 is rotated, pulley system 242 causes proximal gear 242 to rotate as well. As a result, both gear 144 of rotatable knob 140 and proximal gear 240 can cause tubular rack 118 to be retracted when rotatable knob 140 is rotated. This arrangement can ensure that rotation of rotatable knob 140 continues to retract tubular rack 118 for a period of time after the portion of tubular rack 118 including teeth 122 has been retracted proximally beyond rotatable knob 140.

As an alternative to or in addition to the rotatable knob arrangements discussed above, rotatable knob 140 can be positioned nearer proximal end 128 of handle assembly 104. This arrangement can increase the length of tubular rack 118 that engages rotatable knob 140 during retraction.

As a further example, while the stent deployment methods described above include retracting tubular rack 118 and outer sheath 120 by rotating rotatable knob 140 and then pulling proximally on pull grip 126, other techniques can be used. In some embodiments, for example, tubular rack 118 and outer sheath 120 are retracted by pulling proximally on pull grip 126 only. Alternatively, tubular rack 118 and outer sheath 120 can be retracted by rotating rotatable knob 140 only. In certain embodiments, tubular rack 118 and outer sheath 120 are retracted for an initial distance by pulling proximally on pull grip 126 and then retracted the remaining distance by rotating rotatable knob 140.

Figure 9:
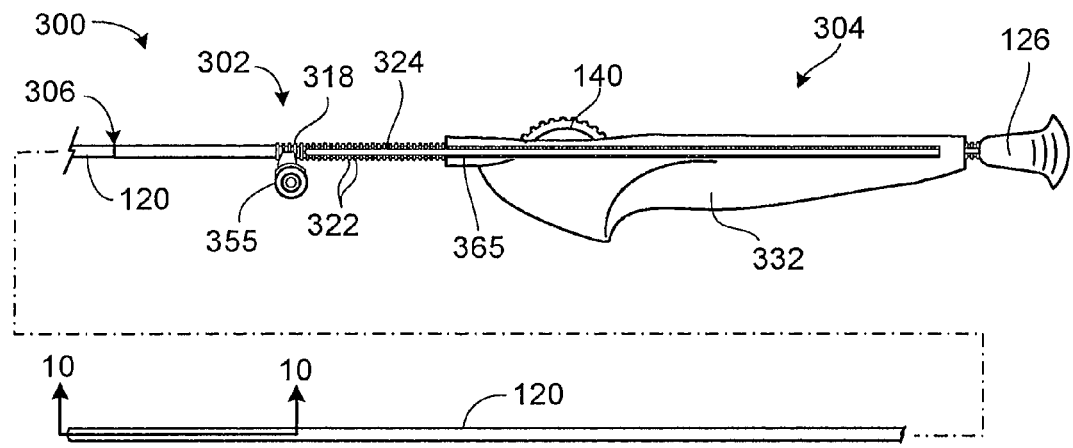
FIG. 9 is a broken, side view of a stent delivery system.
Figure 10:
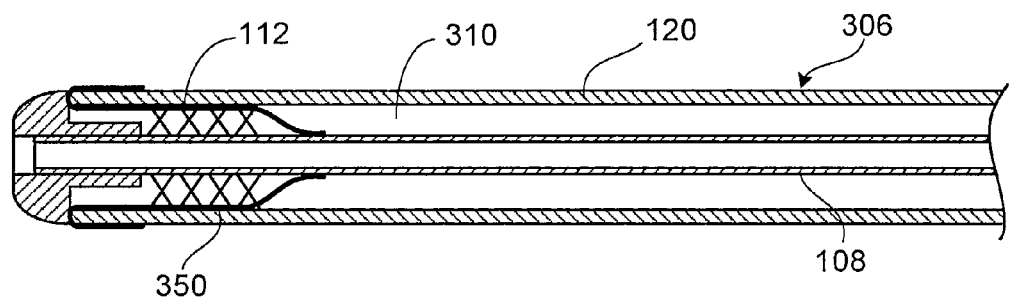
FIG. 10 is a cross-sectional view of a distal region of the catheter assembly of the stent delivery system of FIG. 9, taken along line 10-10 in FIG. 1.

Referring to FIGS. 9 and 10, another stent delivery system 300 includes a catheter assembly 302 and a handle assembly 304. Catheter assembly 302 includes an outer tubular assembly 306, which includes a tubular rack 318 and outer sheath 120. Inner tubular member 108 extends through a lumen 310 formed by outer tubular assembly 306. Stent 112 is disposed between outer tubular assembly 306 and inner tubular member 108, near the distal ends of outer tubular assembly 306 and inner tubular member 108. A membrane 350 is disposed between inner tubular member 108 and outer sheath 120. A proximal end portion of membrane 350 is attached to the outer surface of inner tubular member 108 at a location slightly proximal to stent 112. A distal end portion of membrane 350 wraps around the distal end of outer sheath 120 and is attached to the outer surface of a distal portion of outer sheath 120. Thus, when outer sheath 120 is in a fully distal position, as shown in FIG. 10, membrane 350 is disposed between outer sheath 120 and stent 112.

Figure 11:
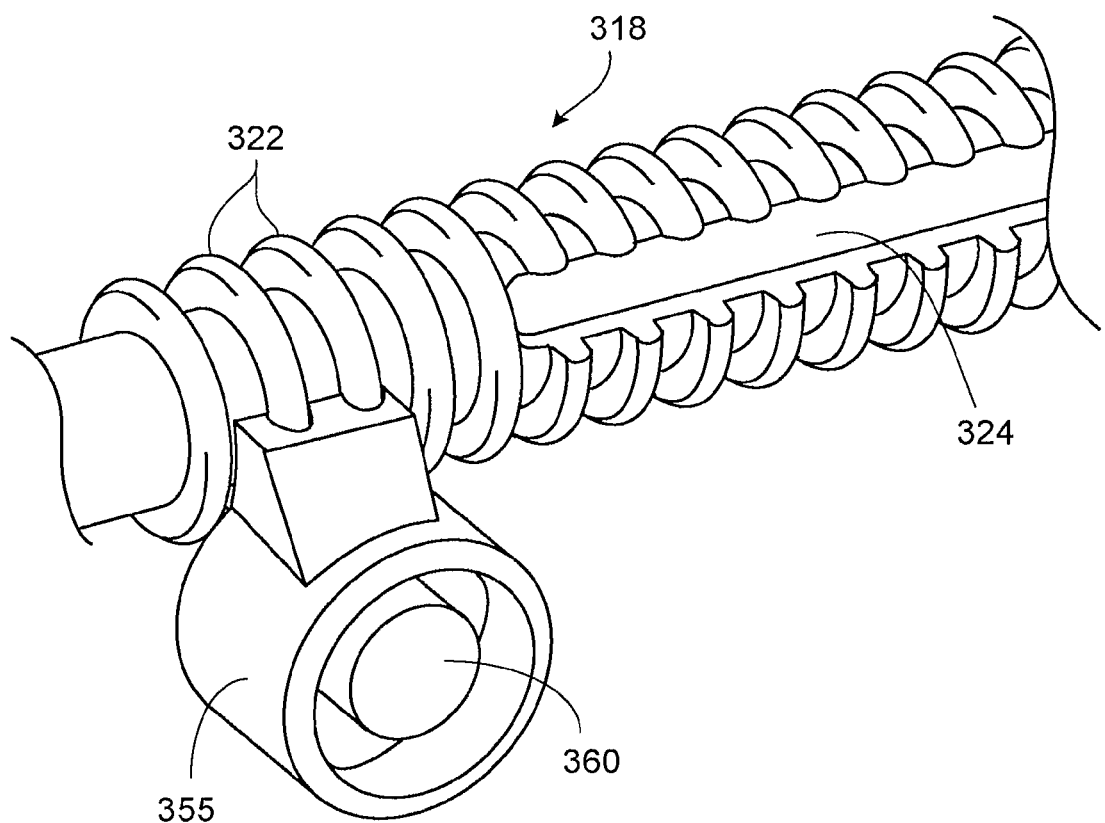
FIG. 11 is a partial, perspective view of a distal region of the rack of the stent delivery system of FIG. 9.

Referring to FIGS. 9 and 11, a fitting 355 extends radially from a distal region of tubular rack 318. Fitting 355 forms a port 360 that is in fluid communication with lumen 310 of outer tubular assembly 306. A seal (e.g., an o-ring) is disposed within lumen 310 proximal to fitting 355. The seal helps to ensure that fluid introduced into lumen 310 via fitting 355 is forced in the distal direction toward membrane 350 and inhibits the fluid from flowing proximally through tubular rack 118. Handle assembly 304 includes a housing 332 that forms a slot 365 configured to receive fitting 355. Slot 365 terminates slightly distal to the proximal end of handle assembly 304. The combination of slot 324 in tubular rack 318 and slot 365 in housing 332 allows the distal end portion of tubular rack 318 to be retracted proximally into housing 332 and allows the proximal end portion of tubular rack 318 to be retracted proximally beyond the proximal end of handle assembly 304.

System 300 is used in a similar manner to system 100. For example, during use, system 300 is navigated through a blood vessel until the stent-carrying portion of catheter assembly 302 is positioned within a desired region of a blood vessel. After positioning the stent-carrying portion of catheter assembly 302 within the desired region of the blood vessel, fluid is passed through lumen 310 of outer tubular assembly 306 toward membrane 350. To introduce the fluid into lumen 310, a hose extending from a pressurized fluid mechanism is secured to fitting 355 and the pressurized fluid mechanism is activated. Tubular rack 318 and outer sheath 120 are then retracted. As tubular rack 318 and outer sheath 120 are retracted a short distance, a pressurized double-layered portion of membrane 350 will surround stent 112. Tubular rack 318 and outer sheath 120 are further retracted until membrane 350 has travelled to a position proximal to the proximal end of stent 112, allowing stent 112 to fully expand within the blood vessel. Slot 324 in tubular rack 318 allows tubular rack 318 to pass through handle assembly 304 in a manner similar to that discussed above with regard to system 100. As tubular rack 118 is retracted, fitting 355, which extends radially from tubular rack 318, travels through slot 365 of housing 332 of handle assembly 304. The combination of slot 324 in tubular rack 318 and slot 365 in housing 332 of handle assembly 304 allows tubular rack 318 to be retracted into handle assembly 304 a sufficient distance to fully deploy stent 112. Tubular rack 118 can, for example, be retracted until the distal end of slot 324 contacts the member that secures inner tubular member 108 to housing 332 of handle assembly 304 and/or until fitting 355 contacts the proximal end of slot 365 in housing 332.

Due to the arrangement of membrane 350 between inner tubular member 108 and outer sheath 120, tubular rack 318 and outer sheath 120 are generally required to be retracted a further overall distance in the proximal direction before stent 112 is fully deployed as compared to systems that include no such membrane, such as system 100 above. Thus, slot 324 of tubular rack 318 and slot 365 of housing 332 of handle assembly 304 are particularly beneficial to system 300 as they allow the proximal end of tubular rack 318 to be retracted to a location proximal to the proximal end of handle assembly 304 and allow outer sheath 120 to be retracted into handle assembly 104. This arrangement enables the overall length of the system to be reduced.

In addition to being used as a conduit to inject fluid into lumen 310 of outer tubular assembly 306, fitting 355 can be used as a pull grip. If desired, for example, the user can pull proximally on fitting 355 to cause the retraction of tubular rack 318 and outer sheath 120. Thus, fitting 355 can be used as an alternative to or in addition to pull grip 126. In some embodiments, the system is provided only with fitting 355 and no pull grip at the proximal end of tubular rack 318.

As an additional example, while systems 100 and 300 have been described as being used to deliver and deploy self-expanding stents, in certain embodiments, the systems can be used to deliver and deploy other types of implantable medical endoprostheses, such as balloon expandable stents, stent-grafts, and filters (e.g., arterial and venous filters).

As another example, while systems 100 and 300 have been described as being used in various different types of blood vessels, the systems can alternatively or additionally be used in other types of body vessels.

Other embodiments are in the claims.

What is claimed is:

1. A system, comprising:
a connector secured to a housing of a handle assembly;
an inner member secured to the connector; and
an outer member at least partially surrounding the inner member, the outer member including a sheath portion and a tubular rack portion secured to the sheath portion, the tubular rack portion having a longitudinal slot formed therein, wherein a portion of the connector is disposed within the slot, wherein the tubular rack portion is capable of longitudinally shifting relative to the connector, the outer member and the inner member being configured so that an implantable medical endoprosthesis can be disposed between the outer member and the inner member; and
wherein a proximal end of the tubular rack portion extends proximally through a proximal end of the handle assembly and the proximal end of the tubular rack portion extends proximally from the proximal end of the handle assembly.

2. The system of claim 1, wherein the outer member is retractable relative to the inner member.

3. The system of claim 2, wherein a distal end of the slot, upon contacting the connector, substantially prevents further retraction of the outer member relative to the inner member.

4. The system of claim 2, further comprising a stop secured to the outer member, the stop being configured to contact the connector so that displacement of the outer member and the inner member can be limited.

5. The system of claim 1, wherein the tubular rack portion comprises radially extending teeth.

6. The system of claim 5, wherein the handle assembly comprises a rotatable knob configured to engage the radially extending teeth such that the outer member can be retracted by rotating the rotatable knob.

7. The system of claim 5, wherein the slot extends from the proximal end of the tubular rack portion to a location proximal to a distal end of the tubular rack portion.

8. The system of claim 5, wherein the slot extends from the proximal end of the tubular rack portion to a distal end of the tubular rack portion.

9. The system of claim 8, wherein the slot extends into the sheath portion.

10. The system of claim 1, wherein the sheath portion and the inner member are configured so that an implantable medical endoprosthesis can be disposed between the sheath portion and the inner member.

11. The system of claim 1, wherein at least a portion of the sheath portion can be retracted into the handle assembly.

12. The system of claim 1, wherein a pull grip is secured to the proximal end of the tubular rack portion proximal to the handle assembly.

13. The system of claim 1, wherein the connector comprises a tubular portion at least partially surrounding the inner member.

14. The system of claim 13, wherein the connector further comprises a rib portion securing the tubular portion to the handle assembly, the slot being configured so that the rib portion of the connector can extend radially through the slot.

15. The system of claim 1, wherein the slot is configured so that a guide wire can pass radially through the slot.

16. The system of claim 15, wherein, during use, the guide wire passes radially through the slot at a location proximal to the handle assembly.

17. The system of claim 1, further comprising an implantable medical endoprosthesis disposed between the outer member and the inner member.

18. The system of claim 17, wherein the implantable medical endoprosthesis comprises a self-expanding stent.

19. The system of claim 1, wherein the system further comprises a membrane having a first portion attached to the inner member and a second portion attached to the outer member, the membrane at least partially surrounding an implantable medical endoprosthesis disposed between the outer member and the inner member.

20. The system of claim 1, wherein the housing of the handle assembly defines a slot configured to receive a member extending radially from the outer member.

21. The system of claim 20, wherein the member defines a port in fluid communication with a lumen defined between the inner member and the outer member.

* * * * *